US012692545B2

(12) United States Patent
Lu et al.

(10) Patent No.: US 12,692,545 B2
(45) Date of Patent: Jul. 28, 2026

(54) COMBINED AUXILIARY DIAGNOSTIC METHOD, KIT, SYSTEM AND USE OF POINT MUTATION AND METHYLATION OF BLADDER CANCER DRIVER GENES

(71) Applicant: Hunan Yearth Biotechnological Co, LTD, Hunan (CN)

(72) Inventors: Li Lu, Hunan (CN); Genming Xu, Hunan (CN); Qian Zhao, Hunan (CN)

( * ) Notice: Subject to any disclaimer, the term of this patent is extended or adjusted under 35 U.S.C. 154(b) by 397 days.

(21) Appl. No.: 17/298,299

(22) PCT Filed: Mar. 11, 2020

(86) PCT No.: PCT/CN2020/078811
§ 371 (c)(1),
(2) Date: May 28, 2021

(87) PCT Pub. No.: WO2021/073029
PCT Pub. Date: Apr. 22, 2021

(65) Prior Publication Data
US 2022/0259664 A1     Aug. 18, 2022

(30) Foreign Application Priority Data
Oct. 17, 2019    (CN) ........................ 201910988473.X

(51) Int. Cl.
*C12Q 1/6886*       (2018.01)

(52) U.S. Cl.
CPC ..... *C12Q 1/6886* (2013.01); *C12Q 2600/154* (2013.01); *C12Q 2600/156* (2013.01)

(58) Field of Classification Search
CPC ............ C12Q 1/6886; C12Q 2600/154; C12Q 2600/156; Y02A 50/30
See application file for complete search history.

(56) References Cited

U.S. PATENT DOCUMENTS

2013/0224738 A1   8/2013   Scher et al.
2019/0106735 A1   4/2019   Lim et al.

FOREIGN PATENT DOCUMENTS

| EP | 1491639 A2 * | 12/2004 | ........... C12Q 1/6827 |
| WO | 2013116705 A1 | 8/2013 | |
| WO | 2013173478 A1 | 11/2013 | |
| WO | 2015049063 A1 | 4/2015 | |
| WO | 2016138105 A2 | 9/2016 | |
| WO | 2016141324 A2 | 9/2016 | |
| WO | 2017067477 A1 | 4/2017 | |

OTHER PUBLICATIONS

Machine Translation of EP 1491639 A2. (Year: 2004).*
GenBank Accession #AF487554 (Year: 2016).*
GenBank Accession #AF098956 (Year: 2016).*
GenBank Accession #AL592546.7 (Year: 2012).*
PLEKHS1 NCBI gene page (Year: 2024).*
Zymo Research, "EZ DNA Methylation-Gold Kit". (Year: 2024).*
Pignot, Plekhsi et al., "A New Molecular Marker Predicting risk of Progression of Non-Muscle-invasive bladder Cancer" Oncology Letters, 02.8, pp. 1-10, Aug. 2, 2019.
Dudley, Jonathan et al., "Detection and Surveillance of Bladder Cancer using Urine Tumor DNA" Cancer Discov. 21-12, pp. 500-509, Apr. 2019.

* cited by examiner

*Primary Examiner* — Angela M. Bertagna
*Assistant Examiner* — Francesca Filippa Giammona
(74) *Attorney, Agent, or Firm* — The Rapacke Law Group, P.A.

(57) ABSTRACT

Disclosed are the method, kit, system and use for screening or detecting or assisting in the diagnosis of bladder cancer, which are able to simultaneously detect FGFR3, TERT, PLEKHS1 point mutations and OTX1, NID2 and NRN1 methylation levels, thereby realizing the combined detection of gene point mutation and methylation, reducing the demand for samples, experimental operation steps and detection cycle, and improving the specificity and sensitivity of detection.

3 Claims, No Drawings
Specification includes a Sequence Listing.

SEQUENCE LISTING

<160> NUMBER OF SEQ ID NOS: 43

<210> SEQ ID NO 1
<211> LENGTH: 234
<212> TYPE: DNA
<213> ORGANISM: Artificial Sequence
<220> FEATURE:
<223> OTHER INFORMATION: Point mutation detection template

<400> SEQUENCE: 1
gtgctgggtg agggccctgg ggcggcgcgg gggtgggggc ggcagtggcg gtggtggtga        60
gggagggggt ggcccctgag cgtcatctgc ccccacagag cgctccccgc accggcccat       120
cctgcaggcg gggctgccgg ccaaccagac ggcggtgctg ggcagcgacg tggagttcca       180
ctgcaaggtg tacagtgacg cacagcccca catccagtgg ctcaagcacg tgga            234

<210> SEQ ID NO 2
<211> LENGTH: 225
<212> TYPE: DNA
<213> ORGANISM: Artificial Sequence
<220> FEATURE:
<223> OTHER INFORMATION: Point mutation detection template

<400> SEQUENCE: 2
gcttcccacg tgcgcagcag gacgcagcgc tgcctgaaac tcgcgccgcg aggagagggc        60
ggggccgcgg aaaggaaggg gaggggctgg gagggcccgg agggggctgg gccggggacc       120
cgggaggggt cgggacgggg cggggtccgc gcggaggagg cggagctgga aggtgaaggg       180
gcaggacggg tgcccgggtc cccagtccct ccgccacgtg ggaag                     225

<210> SEQ ID NO 3
<211> LENGTH: 204
<212> TYPE: DNA
<213> ORGANISM: Artificial Sequence
<220> FEATURE:
<223> OTHER INFORMATION: Point mutation detection template

<400> SEQUENCE: 3
gagcactgga ccagcgacct cttggcttcc agtaagtact gcttggtgta tctggtttgg        60
acttccaagg ctgggatgat ctagaagctt ttttgcaatt gaacaattgc aaaattggaa       120
atggaaaatt ttgcagatat gctgtatttc tgttatgggc actttcttca taagcttcct       180
aggctatact atagtcagag ggaa                                            204

<210> SEQ ID NO 4
<211> LENGTH: 360
<212> TYPE: DNA
<213> ORGANISM: Artificial Sequence
<220> FEATURE:
<223> OTHER INFORMATION: Methylation site template

<400> SEQUENCE: 4
cgtttggagg tttttttgatt tgttttttata tttaattttg tgtaaatttt ttatttcgtt       60
tgtcggggtg ggggagtggg ggagattaga aataaggggg agaaattttt cgaaagggaa       120
taaagtgttt aatttttagg aggaggtgtt atttaaaaga ttcgtttagt ttagagttgg       180
tttcgggtgg gaaatgggtt tcgttcgtac gaataattcg gggaaatcgt tttaaggagg       240 attttttacgt agtatgtgga aaaaagttga gggtaggggt ttgtggttat attttttatt       300
aaaaagtttt tgttagaggt agtttaagaa agagagagaa agagcgaaaa agaaattttt       360

-continued

```
<210> SEQ ID NO 5
<211> LENGTH: 360
<212> TYPE: DNA
<213> ORGANISM: Artificial Sequence
<220> FEATURE:
<223> OTHER INFORMATION: Methylation site template

<400> SEQUENCE: 5
gtagtggtta ttatatttgg ttttcgttaa ttttttttaag gtagcggtcg ttggagtagc      60
ggggttggcg gggtaaaagt ttttggttag ggttgtttgg agttgttttt tttatttcgt     120
ttttagggag ttttcgggtt attttttttat tcgggttgtt tcgcggtttt taaggagttt     180
tattttcggg attaaatggt tcgtaaggtt tggggtagcg gcgttgtagg agatgagttt     240
agcgtaaagg gaatttcgta gcggcgagtg cggttgttgg tttgcgcgtt gtggttttaa     300
taggttggta gggcgcgggc gggtggcggg gttgcggtat gagttttgtt ttttgtttttg     360

<210> SEQ ID NO 6
<211> LENGTH: 343
<212> TYPE: DNA
<213> ORGANISM: Artificial Sequence
<220> FEATURE:
<223> OTHER INFORMATION: Methylation site template

<400> SEQUENCE: 6
tcgggaggat cggatatttt aattttttcgg tttttaacgc gggcgtttgt tcgcgagcgt      60
cgggttagac gtcgaagagg aaggtgatcg aattcgtagt agttttcgag agcgtattcg     120
tttgtaaatt gttgtaggaa gagcgaggcg ggttttgcgt tttttaattc ggaacgggaa     180
gtattgggga agggatcgag gttaatttcg attttcgttg gggtagatac gtaaattttt     240
ttaaattttc gagtttattt tatagcgaat attaaatatt tttgcgatta taatattaat     300
aaatcgaata ttgacgtaaa attttaagaa taaacgaatt ttt                       343

<210> SEQ ID NO 7
<211> LENGTH: 28
<212> TYPE: DNA
<213> ORGANISM: Artificial Sequence
<220> FEATURE:
<223> OTHER INFORMATION: FGFR3-ARMS-F1

<400> SEQUENCE: 7
gagcgttatt tgttttttata gagcgttg                                         28

<210> SEQ ID NO 8
<211> LENGTH: 31
<212> TYPE: DNA
<213> ORGANISM: Artificial Sequence
<220> FEATURE:
<223> OTHER INFORMATION: FGFR3-ARMS-F2

<400> SEQUENCE: 8
ttgagcgtta tttgttttta tagagcgttg t                                     31

<210> SEQ ID NO 9
<211> LENGTH: 30
<212> TYPE: DNA
<213> ORGANISM: Artificial Sequence
<220> FEATURE:
<223> OTHER INFORMATION: FGFR3-ARMS-F3

<400> SEQUENCE: 9
gagcgttatt tgttttttata gagcgttgtt                                       30
```

-continued

```
<210> SEQ ID NO 10
<211> LENGTH: 28
<212> TYPE: DNA
<213> ORGANISM: Artificial Sequence
<220> FEATURE:
<223> OTHER INFORMATION: FGFR3-ARMS-F4

<400> SEQUENCE: 10
gagcgttatt tgtttttata gagcggtg                                        28

<210> SEQ ID NO 11
<211> LENGTH: 28
<212> TYPE: DNA
<213> ORGANISM: Artificial Sequence
<220> FEATURE:
<223> OTHER INFORMATION: FGFR3-ARMS-R

<400> SEQUENCE: 11
taaaactata cgtcactata caccttac                                        28

<210> SEQ ID NO 12
<211> LENGTH: 32
<212> TYPE: DNA
<213> ORGANISM: Artificial Sequence
<220> FEATURE:
<223> OTHER INFORMATION: FGFR3-ARMS-FAM

<400> SEQUENCE: 12
cgtatcggtt tattttgtag gcggggttgt cg                                   32

<210> SEQ ID NO 13
<211> LENGTH: 25
<212> TYPE: DNA
<213> ORGANISM: Artificial Sequence
<220> FEATURE:
<223> OTHER INFORMATION: TERT-ARMS-F1

<400> SEQUENCE: 13
gagggggttg ggtcggggat tcgga                                           25

<210> SEQ ID NO 14
<211> LENGTH: 22
<212> TYPE: DNA
<213> ORGANISM: Artificial Sequence
<220> FEATURE:
<223> OTHER INFORMATION: TERT-ARMS-F2

<400> SEQUENCE: 14
gggttgggtc ggggattcgg aa                                              22

<210> SEQ ID NO 15
<211> LENGTH: 22
<212> TYPE: DNA
<213> ORGANISM: Artificial Sequence
<220> FEATURE:
<223> OTHER INFORMATION: TERT-ARMS-F3

<400> SEQUENCE: 15
ggttgggtcg gggattcgga ag                                              22

<210> SEQ ID NO 16
<211> LENGTH: 25
<212> TYPE: DNA
<213> ORGANISM: Artificial Sequence
<220> FEATURE:
<223> OTHER INFORMATION: TERT-ARMS-F4
```

-continued

```
<400> SEQUENCE: 16 gaggggggttg ggtcgggggat tctga                                          25

<210> SEQ ID NO 17
<211> LENGTH: 24
<212> TYPE: DNA
<213> ORGANISM: Artificial Sequence
<220> FEATURE:
<223> OTHER INFORMATION: TERT-ARMS-R

<400> SEQUENCE: 17
ccgaacaccc gtcctacccc ttca                                             24

<210> SEQ ID NO 18
<211> LENGTH: 22
<212> TYPE: DNA
<213> ORGANISM: Artificial Sequence
<220> FEATURE:
<223> OTHER INFORMATION: TERT-ARMS-HEX

<400> SEQUENCE: 18
tcgggacggg gcggggttcg cg                                               22

<210> SEQ ID NO 19
<211> LENGTH: 27
<212> TYPE: DNA
<213> ORGANISM: Artificial Sequence
<220> FEATURE:
<223> OTHER INFORMATION: PLEKHS1-ARMS-F1

<400> SEQUENCE: 19
gatgatttag aagttttttt gtaatta                                          27

<210> SEQ ID NO 20
<211> LENGTH: 28
<212> TYPE: DNA
<213> ORGANISM: Artificial Sequence
<220> FEATURE:
<223> OTHER INFORMATION: PLEKHS1-ARMS-F2

<400> SEQUENCE: 20
gatgatttag aagttttttt gtaattaa                                         28

<210> SEQ ID NO 21
<211> LENGTH: 30
<212> TYPE: DNA
<213> ORGANISM: Artificial Sequence
<220> FEATURE:
<223> OTHER INFORMATION: PLEKHS1-ARMS-F3

<400> SEQUENCE: 21
ggatgattta gaagtttttt tgtaattaaa                                       30

<210> SEQ ID NO 22
<211> LENGTH: 27
<212> TYPE: DNA
<213> ORGANISM: Artificial Sequence
<220> FEATURE:
<223> OTHER INFORMATION: PLEKHS1-ARMS-F4

<400> SEQUENCE: 22
gatgatttag aagttttttt gtaagta                                          27

<210> SEQ ID NO 23
```

```
<211> LENGTH: 31
<212> TYPE: DNA
<213> ORGANISM: Artificial Sequence
<220> FEATURE:
<223> OTHER INFORMATION: PLEKHS1-ARMS-R

<400> SEQUENCE: 23
cttataaaaa aaatacccat aacaaaaata c                                        31

<210> SEQ ID NO 24
<211> LENGTH: 32
<212> TYPE: DNA
<213> ORGANISM: Artificial Sequence
<220> FEATURE:
<223> OTHER INFORMATION: PLEKHS1-ARMS-ROX

<400> SEQUENCE: 24
taaaattgga atggaaaat tttgtagata tg                                        32

<210> SEQ ID NO 25
<211> LENGTH: 23
<212> TYPE: DNA
<213> ORGANISM: Artificial Sequence
<220> FEATURE:
<223> OTHER INFORMATION: OTX1-bis-ARMS-F1

<400> SEQUENCE: 25
cgtttagttt agagttggtt tcg                                                 23

<210> SEQ ID NO 26
<211> LENGTH: 20
<212> TYPE: DNA
<213> ORGANISM: Artificial Sequence
<220> FEATURE:
<223> OTHER INFORMATION: OTX1-bis-ARMS-F2

<400> SEQUENCE: 26
agtttagagt tggtttcggg                                                     20

<210> SEQ ID NO 27
<211> LENGTH: 25
<212> TYPE: DNA
<213> ORGANISM: Artificial Sequence
<220> FEATURE:
<223> OTHER INFORMATION: OTX1-bis-ARMS-R1

<400> SEQUENCE: 27
ctacgtaaaa atcctcctta aaacg                                               25

<210> SEQ ID NO 28
<211> LENGTH: 24
<212> TYPE: DNA
<213> ORGANISM: Artificial Sequence
<220> FEATURE:
<223> OTHER INFORMATION: OTX1-bis-ARMS-R2

<400> SEQUENCE: 28
ctacgtaaaa atcctcctta aaac                                                24

<210> SEQ ID NO 29
<211> LENGTH: 25
<212> TYPE: DNA
<213> ORGANISM: Artificial Sequence
<220> FEATURE:
<223> OTHER INFORMATION: OTX1-bis-ARMS-R3

<400> SEQUENCE: 29
```

-continued ctacgtaaaa atcctcctta aatcg                                          25

<210> SEQ ID NO 30
<211> LENGTH: 23
<212> TYPE: DNA
<213> ORGANISM: Artificial Sequence
<220> FEATURE:
<223> OTHER INFORMATION: OTX1-bis-ARMS-FAM

<400> SEQUENCE: 30
atgggtttcg ttcgtacgaa taa                                            23

<210> SEQ ID NO 31
<211> LENGTH: 22
<212> TYPE: DNA
<213> ORGANISM: Artificial Sequence
<220> FEATURE:
<223> OTHER INFORMATION: NID2?Cbis-ARMS-F1

<400> SEQUENCE: 31
ggttagggtt gtttggagtt gt                                             22

<210> SEQ ID NO 32
<211> LENGTH: 25
<212> TYPE: DNA
<213> ORGANISM: Artificial Sequence
<220> FEATURE:
<223> OTHER INFORMATION: NID2?Cbis-ARMS-R1

<400> SEQUENCE: 32
caaaccttac gaaccattta atccc                                          25

<210> SEQ ID NO 33
<211> LENGTH: 25
<212> TYPE: DNA
<213> ORGANISM: Artificial Sequence
<220> FEATURE:
<223> OTHER INFORMATION: NID2?Cbis-ARMS-R2

<400> SEQUENCE: 33
caaaccttac gaaccattta atacc                                          25

<210> SEQ ID NO 34
<211> LENGTH: 25
<212> TYPE: DNA
<213> ORGANISM: Artificial Sequence
<220> FEATURE:
<223> OTHER INFORMATION: NID2?Cbis-ARMS-R3

<400> SEQUENCE: 34
caaaccttac gaaccattta atcac                                          25

<210> SEQ ID NO 35
<211> LENGTH: 28
<212> TYPE: DNA
<213> ORGANISM: Artificial Sequence
<220> FEATURE:
<223> OTHER INFORMATION: NID2?Cbis-ARMS-HEX

<400> SEQUENCE: 35
cgggttgttt cgcgcggttt ttaaggag                                       28

<210> SEQ ID NO 36
<211> LENGTH: 25
<212> TYPE: DNA

-continued

```
<213> ORGANISM: Artificial Sequence
<220> FEATURE:
<223> OTHER INFORMATION: NRN1-bis-ARMS-F1

<400> SEQUENCE: 36
gtttgtaaat tgttgtagga agcgc                                          25

<210> SEQ ID NO 37
<211> LENGTH: 25
<212> TYPE: DNA
<213> ORGANISM: Artificial Sequence
<220> FEATURE:
<223> OTHER INFORMATION: NRN1-bis-ARMS-ROX

<400> SEQUENCE: 37
atcgaaatta acctcgatcc cttcc                                          25

<210> SEQ ID NO 38
<211> LENGTH: 23
<212> TYPE: DNA
<213> ORGANISM: Artificial Sequence
<220> FEATURE:
<223> OTHER INFORMATION: NRN1-bis-ARMS-R2

<400> SEQUENCE: 38
atattcgcta taaataaac ccg                                             23

<210> SEQ ID NO 39
<211> LENGTH: 22
<212> TYPE: DNA
<213> ORGANISM: Artificial Sequence
<220> FEATURE:
<223> OTHER INFORMATION: NRN1-bis-ARMS-R3

<400> SEQUENCE: 39
cgtttattct taaaattttc cg                                             22

<210> SEQ ID NO 40
<211> LENGTH: 26
<212> TYPE: DNA
<213> ORGANISM: Artificial Sequence
<220> FEATURE:
<223> OTHER INFORMATION: NRN1-bis-ARMS-R1

<400> SEQUENCE: 40
ataatcgcaa aaatatttaa tatccg                                         26

<210> SEQ ID NO 41
<211> LENGTH: 26
<212> TYPE: DNA
<213> ORGANISM: Artificial Sequence
<220> FEATURE:
<223> OTHER INFORMATION: ATCB-BIS-F2

<400> SEQUENCE: 41
agtgagaaag ggtgtagttt tgggag                                         26

<210> SEQ ID NO 42
<211> LENGTH: 33
<212> TYPE: DNA
<213> ORGANISM: Artificial Sequence
<220> FEATURE:
<223> OTHER INFORMATION: ATCB-BIS-R3

<400> SEQUENCE: 42
ccacaaaaaa ataacccaaa taaataaccc act                                 33
```

-continued

```
<210> SEQ ID NO 43
<211> LENGTH: 33
<212> TYPE: DNA
<213> ORGANISM: Artificial Sequence
<220> FEATURE:
<223> OTHER INFORMATION: ATCB-VIC

<400> SEQUENCE: 43
cctcttctaa taaccacctc cctccttcct aac                                    33
```

COMBINED AUXILIARY DIAGNOSTIC METHOD, KIT, SYSTEM AND USE OF POINT MUTATION AND METHYLATION OF BLADDER CANCER DRIVER GENES

CROSS REFERENCE TO RELATED APPLICATION

This patent application claims the benefit and priority of Chinese Patent Application NO. 201910988473.X entitled "Combined auxiliary diagnostic method, kit, system and use of point mutation and methylation of bladder cancer driver genes" filed on Oct. 17, 2019, the disclosure of which is incorporated by reference herein in its entirety as part of the present application.

TECHNICAL FIELD

The present disclosure belongs to the technical field of gene mutation detection, and particularly relates to a method for simultaneously detecting DNA methylation and single nucleotide polymorphism of bladder cancer driver genes, a related kit, a system and use thereof.

BACKGROUND ART

Bladder cancer is the most common malignant tumor of urinary system, ranking the sixth in the incidence of male tumors in China. Among them, the incidence rate of male is 3-4 times that of female, while the mortality rate of female is higher than that of male. Bladder cancer becomes an adult cancer with the highest diagnosis and treatment cost due to the need for continuous follow-up and high recurrence rate after surgery (the recurrence rate of non muscle-invasive bladder cancer can reach 60-70%).

Poor prognosis and easy recurrence are important characteristics of bladder cancer, and effective treatment largely depends on early diagnosis and early treatment of bladder cancer. However, the incidence of early bladder cancer is asymptomatic, and most patients only go to the hospital because of hematuria under the naked eye or microscope, and they have already been at an advanced stage of cancer at that time. Therefore, it is of great clinical value to find a specific early diagnosis method for bladder cancer. Cystoscopy, as the gold standard for the diagnosis of bladder cancer, has a missed diagnosis rate of up to 10%, and it is an invasive examination with low acceptance. Urine cytology has high sensitivity to high-grade bladder cancer, but low detection rate to low-grade bladder cancer. Imaging tests may detect larger tumors in the bladder. However, none of the traditional bladder cancer examination methods mentioned above can meet the requirements of non-invasive and high detection rate at the same time.

Although molecular diagnostic methods can diagnose bladder cancer in clinic at present, they are all singly used. For example, the method is only for detecting gene methylation or single point mutation and other relevant biological information. The accuracy and sensitivity of its detection rate are still unsatisfactory.

In view of the above problems, the combined detection of point mutation and methylation of driver gene is used for the first time in the present disclosure to diagnose bladder cancer, improving the shortcoming of single detection of the current detection method, comprehensively evaluating the negative and positive of detection samples from multiple dimensions, and greatly expanding the detection area, and thus screening bladder cancer tumorigenesis at an early stage. Therefore, the development of diagnostic technology based on this product is of great significance for preventing bladder cancer and monitoring postoperative recurrence.

SUMMARY OF THE INVENTION

In view of this, the purpose of the present disclosure is to provide a method for simultaneously detecting DNA methylation and single nucleotide polymorphism of bladder cancer driver genes, a related kit, a system and use thereof. The detection method, related kit and system have characterized with good sensitivity and high accuracy, and greatly improve the detection rate of bladder cancer in the early stage.

In order to achieve the purpose of the present disclosure, the present disclosure provides a detection method for screening bladder cancer by targeting genes related to the pathway of bladder cancer, which comprises the detection for targeting gene point mutation and/or methylation level of gene expression regulatory region. In some embodiments, the detection method is the combined detection for targeting gene point mutation and methylation level of gene regulatory region.

In some embodiments, the genes for detecting point mutation include one or more combinations of FGFR3, TERT and PLEKHS1. In some embodiments, the region to be detected for point mutation in FGFR3 is set forth in SEQ ID NO: 1; the region to be detected for TERT point mutation is set forth in SEQ ID NO: 2; and the region to be detected for PLEKHS1 point mutation is set forth in SEQ ID NO: 3. In some embodiments, the genes for detecting the methylation level in regulatory region include one or more combinations of OTX1, NID2 and NRN1. In some embodiments, the region to be detected for OTX1 methylation level is set forth in SEQ ID NO: 4; the region to be detected for NID2 methylation level is set forth in SEQ ID NO: 5; the region to be detected for NRN1 methylation level is set forth in SEQ ID NO: 6.

In some embodiments, the detection method also includes the detection of internal reference genes. In some embodiments, the internal reference gene is ATCB. In some embodiments, the primers and probe of ATCB are the sequences set forth in SEQ ID NO: 41-SEQ ID NO: 43.

The present disclosure also provides a detection reagent for screening bladder cancer by targeting genes related to the pathway of bladder cancer, which comprises specific primers and probes designed for a template of the region to be detected, detecting by using a fluorescent quantitative PCR instrument through a PCR reaction system, thereby realizing the detection for samples.

In some embodiments, the designed specific primers include a forward primer and a reverse primer designed for the region to be detected. In some embodiments, the region to be detected includes point mutation and gene methylation. In some embodiments, the gene methylation sites in the region to be detected include a CpG site. In some embodiments, the point mutation comprises a point mutation for one or more combinations of FGFR3, TERT and PLEKHS1. In some embodiments, the region to be detected for FGFR3 point mutation is the sequence set forth in SEQ ID NO: 1; the region to be detected for TERT point mutation is the sequence set forth in SEQ ID NO: 2; and the region to be detected for PLEKHS1 point mutation is the sequence set forth in SEQ ID NO: 3.

In some embodiments, the gene methylation comprises methylation for one or more combinations of OTX1, NID2 and NRN1.

In some embodiments, the region to be detected for OTX1 methylation is the sequence set forth in SEQ ID NO: 4; the region to be detected for NID2 methylation level is the sequence set forth in SEQ ID NO: 5; the region to be detected for NRN1 methylation level is the sequence set forth in SEQ ID NO: 6.

In some embodiments, the size of the forward primer and the reverse primer amplification of the target region is 80-150 bp, preferably 80-100 bp. In some embodiments, the 3' end of the forward primer or the reverse primer overlap with the site to be detected. In some embodiments, the point to be detected is 0-5 bases away from the 3' end of the forward primer or the reverse primer. In some embodiments, 0-2 base mismatches are introduced into the penultimate position and the antepenultimate position at the 3' end of the detection primer, so as to improve the specificity of the detection mutation template of the primer. In some embodiments, the 0-2 base mismatches of the penultimate primer and the antepenultimate primer at the 3' end of the detection primer follow the mismatch combination of strong mismatch plus weak mismatch or weak mismatch plus strong mismatch combinations. In some embodiments, the strong mismatch base is A/G and C/T. In some embodiments, the weak mismatch base is: A/C and G/T. In some embodiments, the detection primers can be selected from the sequences set forth in SEQ ID NOs: 7-11, 13-17, 19-23, 25-29, 31-34 and 36-39. In some embodiments, the forward primers and reverse primers for FGFR3 point mutation may be selected from any sequence set forth in SEQ ID NOs: 7-10 as well as the sequence set forth in SEQ ID NO: 11, preferably the forward primer and reverse primer are the sequences set forth in SEQ ID NO: 10 and SEQ ID NO: 11, respectively. In some embodiments, the forward primers and reverse primers for TERT point mutation may be selected from any sequence set forth in SEQ ID NOs: 13-16 as well as the sequence set forth in SEQ ID NO: 17; preferably, the forward primer and reverse primer are set forth in SEQ ID NO: 16 and SEQ ID NO: 17 respectively. In some embodiments, the forward primers and reverse primers for PLEKHS1 point mutation are selected from any sequence set forth in SEQ ID NOs: 19-22 as well as the sequence set forth in SEQ ID NO: 23; and preferably the forward primer and reverse primer are the sequences set forth in SEQ ID NO: 22 and SEQ ID NO: 23 respectively. In some embodiments, the forward primers and reverse primers for OTX1 methylation may be selected from any sequence set forth in SEQ ID NOs: 25 and 26 and any of the sequence set forth in SEQ ID NOs: 27-29; preferably the forward primer and reverse primer are the sequences set forth in SEQ ID NO: 25 and SEQ ID NO: 29, respectively. In some embodiments, the forward primers and reverse primers for NID2 methylation may be selected from the sequence set forth in SEQ ID NO: 31 as well as any one of the sequence set forth in SEQ ID NOs: 32-34; preferably the forward primer and reverse primer are the sequences set forth in SEQ ID NO: 31 and SEQ ID NO: 34, respectively. In some embodiments, the forward primers and reverse primers for NRN1 methylation may be selected from the sequences set forth in SEQ ID NO: 36 as well as any of the sequence set forth in SEQ ID NO: 37-39, and preferably the forward primer and reverse primer are the sequences set forth in SEQ ID NO: 36 and SEQ ID NO: 39, respectively. In some embodiments, the probe is close to the site to be detected. In some embodiments, the probe is close to the site to be detected. In some embodiments, the probe reporter fluorophores include one or more probe reporter fluorophores such as FAM, HEX, VIC and ROX. The quenchers include one or more quenchers such as BHQ1, BHQ2, Cy3 and Cy5. In some embodiments, the probe is selected from any sequence set forth in SEQ ID NOs: 12, 18, 24, 30, 35 and 40 or any combination thereof. In some embodiments, the templates of the region to be detected include DNA templates and single-stranded templates after heavy salt transformation; preferably a template after heavy salt transformation. In some embodiments, the heavy salt transformation is carried out by bisulfite. In some embodiments, the structure of the region to be detected is selected from any sequence set forth in SEQ ID NOs: 1-6 or any combination thereof. In some embodiments, the specific primers and probes also include primers and probes designed for internal reference genes. In some embodiments, the internal reference gene is selected from ATCB. In some embodiments, the primer and probe designed for the internal reference gene are set forth in SEQ ID NOs: 41, 42 and 43.

In addition, the present disclosure also provides an efficient and highly specific PCR reaction system for screening bladder cancer by targeting genes related to the pathway of bladder cancer. The PCR reaction system comprises the primers and probes, PCR reaction enzymes and PCR enhancers, which are used for screening bladder cancer by targeting genes related to the pathway of bladder cancer.

In some embodiments, the PCR reaction enzyme is selected from DNA polymerases with 5'-3' exonuclease activity: such as one or more of Taq DNA polymerase, AmpliTaq Gold 360 DNA polymerase and 2G Robust DNA polymerase.

In some embodiments, the PCR enhancer comprises: 1-10 mM DTT, 0.1-10% DMSO and 1-5% glycerol.

In addition, the present disclosure also provides a PCR detection reaction procedure for screening bladder cancer by targeting the genes related to the pathway of bladder cancer, which is used for the detection method and detection reagent for screening bladder cancer by targeting genes related to the pathway of bladder cancer, and the detection procedure comprises three modules: a sample denaturation reaction module, a high TM region template pre-amplification enrichment module and a detection reaction module. In some embodiments, the sample denaturation reaction module realizes the denaturation of the sample into a single chain. In some embodiments, the high TM region template pre-amplification enrichment module preferentially amplifies and enriches the mutant template. In some embodiments, the detection reaction module realizes the collection of PCR and fluorescence signals of the sample, and realizes the detection of the sample.

In some embodiments, the preferred PCR detection reaction procedure is as follows:

| the first stage | 95° C. | 10 min | 1 cycle | pre-denaturation |
|---|---|---|---|---|
| the second stage | 95° C. | 15 s | 15 cycles | high TM template enrichment |
| | 59° C. | 45 s | | |
| | 72° C. | 1 min | | |
| the third stage | 95° C. | 15 s | 35 cycles | |
| | 55° C. | 45 s | | |
| | 72° C. | 1 min | | collection of the fluorescence signal |
| the fourth stage | 40° C. | 1 min | 1 cycle | cooling |

In addition, the present disclosure also provides an auxiliary diagnostic kit for bladder cancer, which comprises a sample nucleic acid extraction reagent module, a nucleic acid DNA heavy salt transformation module and a point mutation and methylation detection module of bladder cancer driver genes. In some embodiments, the sample is preferably a urine sample. In some embodiments, the nucleic acid extraction module is selected from one or more of Genomic DNA Extraction kit (Genmagbio), Free DNA extraction kit (TIANGEN BIOTECH (BEIJING) CO.,LTD) and Genomic DNA Extraction kit (TIANGEN BIOTECH (BEIJING) CO.,LTD). In some embodiments, the heavy salt transformation is carried out by bisulfite. In some embodiments, the nucleic acid DNA heavy salt transformation module is selected from one or more of large-volume nucleic acid heavy salt transformation kit (TIANGEN BIOTECH (BEIJING) CO.,LTD) and nucleic acid heavy salt transformation kit (Zymo Research). In some embodiments, the point mutation and methylation detection module of bladder cancer driver genes comprises the aforementioned detection reagent for screening bladder cancer by targeting the genes related to the pathway of bladder cancer.

In addition, the present disclosure also provides a detection method using the bladder cancer auxiliary diagnosis kit, which comprises the following steps: 1) extracting nucleic acid from the collected samples; 2) distributing the extracted nucleic acid into two parts, one part is used for heavy salt transformation, and the other part is used for gene point mutation detection, carrying out heavy salt transformation by bisulfite on the nucleic acid sample used for heavy salt transformation; 3) respectively detecting the point mutation and gene methylation level of the part used for gene point mutation detection and the part treated by heavy salt transformation; 4) analyzing the negative and positive of the detection results. In some embodiments, the method may also be as follows: 1) extracting the sample nucleic acid; 2) distributing the extracted nucleic acid into two parts, one part is used for heavy salt transformation, and the other part is used for gene point mutation detection; 3) carrying out heavy salt transformation on the nucleic acid sample used for heavy salt transformation; 4) respectively detecting the point mutation and gene methylation level of the part used for gene point mutation detection and the part treated by heavy salt transformation; 5) analyzing the negative and positive of the detection results. In some embodiments, the heavy salt transformation is carried out by bisulfite. In some embodiments, the collected sample is urine.

In addition, the present disclosure also provides a detection system for screening bladder cancer by targeting the genes related to the pathway of bladder cancer, which is used for performing the following steps: 1) extracting the sample nucleic acid; 2) distributing the extracted nucleic acid into a point mutation detection reaction module and a methylation detection reaction module, carrying out heavy salt transformation treatment on the nucleic acid in the methylation detection reaction module; 3) respectively detecting the point mutation and gene methylation level on the point mutation detection reaction module and the methylation detection reaction module treated by heavy salt transformation; 4) analyzing the negative and positive of the detection results. The detection system for screening bladder cancer by targeting the genes which is related to the pathway of bladder cancer may also be a detection system for performing the following steps: 1) extracting the sample nucleic acid; 2) distributing the extracted nucleic acid into a point mutation detection reaction module and a methylation detection reaction module; 3) carrying out heavy salt transformation treatment on the nucleic acid in the methylation detection reaction module; 4) respectively detecting the point mutation and gene methylation level on the point mutation detection reaction module and the methylation detection reaction module treated by heavy salt transformation; 5) analyzing the negative and positive of the detection results. In some embodiments, the sample may be a urine sample. In some embodiments, the detection system also comprises a module for carrying out the internal reference gene detection. In some embodiments, the point mutation genes include one or more combinations of FGFR3, TERT and PLEKHS1. In some embodiments, the methylated genes include one or more combinations of OTX1, NID2 and NRN1. In some embodiments, the point mutation and gene methylation level are detected by specific primers and probes. In some embodiments, the target region by the specific primers and probes is 80-150 bp, preferably 80-100 bp. In some embodiments, the structure of the region to be detected which is targeted by the specific primers and probes is selected from any one of the sequences set forth in SEQ ID NOs: 1-6 or any combination thereof. In some embodiments, the 3' end of the forward primer or the reverse primer overlap with the site to be detected. In some embodiments, the point to be detected is 0-5 bases away from the 3' end of the forward primer or the reverse primer. In some embodiments, 0-2 base mismatches are introduced into the penultimate position and the antepenultimate position at the 3' end of the detection primer, so as to improve the specificity of the detection mutation template of the primer. In some embodiments, the specific primers can be selected from the sequences set forth in SEQ ID NOs: 7-11, 13-17, 19-23, 25-29, 31-34 and 36-39. In some embodiments, the forward primers and reverse primers for FGFR3 point mutation may be selected from any sequence of SEQ ID NOs: 7-10 as well as the sequence set forth in SEQ ID NO: 11, preferably the forward primer and reverse primer are the sequences set forth in SEQ ID NO: 10 and SEQ ID NO: 11, respectively. In some embodiments, the forward primers and reverse primers for TERT point mutation may be selected from any sequence of SEQ ID NOs: 13-16 as well as the sequence set forth in SEQ ID NO: 17, preferably, the forward primer and reverse primer are set forth in SEQ ID NO: 16 and SEQ ID NO: 17 respectively. In some embodiments, the forward primers and reverse primers for PLEKHS1 point mutation are selected from any sequences set forth in SEQ ID NOs: 19-22 as well as SEQ ID NO: 23, and preferably the forward primer and reverse primer are the sequences set forth in SEQ ID NO: 22 and SEQ ID NO: 23 respectively. In some embodiments, the forward primers and reverse primers for OTX1 methylation may be selected from any sequence set forth in SEQ ID NOs: 25 and 26 and any of the sequences shown in SEQ ID NOs: 27-29, preferably the forward primer and reverse primer are the sequences set forth in SEQ ID NO: 25 and SEQ ID NO: 29, respectively. In some embodiments, the forward primers and reverse primers for NID2 methylation may be selected from the sequences set forth in SEQ ID NO: 31 as well as any one of the sequences set forth in SEQ ID NOs: 32-34, preferably the forward primer and reverse primer are the sequences set forth in SEQ ID NO: 31 and SEQ ID NO: 34, respectively. In some embodiments, the forward primers and reverse primers for NRN1 methylation may be selected from the sequences set forth in SEQ ID NO: 36 as well as any of the sequences set forth in SEQ ID NO: 37-39, and preferably the forward primer and reverse primer are the sequences set forth in SEQ ID NO: 36 and SEQ ID NO: 39, respectively. In some embodiments, the probe is close to the site to be detected. In some embodiments, the probe is close to the site to be detected. In some embodiments, the probe reporter fluorophores include one or more probe reporter fluorophores such as FAM, HEX, VIC and ROX. The quenchers include one or more quenchers such as BHQ1, BHQ2, Cy3 and Cy5. In some embodiments, the probe is selected from any sequence set forth in SEQ ID NOs: 12, 18, 24, 30, 35 and 40 or any combination thereof.

In some embodiments, the internal reference gene is ATCB. In some embodiments, the primer and probe designed for the internal reference gene are set forth in SEQ ID NOs: 41, 42 and 43.

In some embodiments, the PCR reaction conditions for detecting the point mutation and the gene methylation level are as follows:

| The first stage | 95° C. | 10 min | 1 cycle | Pre-denaturation |
|---|---|---|---|---|
| The second stage | 95° C. | 15 s | 15 cycles | High TM template |
| | 59° C. | 45 s | | enrichment |
| | 72° C. | 1 min | | |
| The third stage | 95° C. | 15 s | 35 cycles | |
| | 55° C. | 45 s | | |
| | 72° C. | 1 min | | Collection of the fluorescence signal |
| The fourth stage | 40° C. | 1 min | 1 cycle | Cooling |

In addition, the present disclosure also provides use of the primers, probes, detection reagents, diagnostic kits and detection systems in preparing products for diagnosis or auxiliary diagnosis of bladder cancer.

Compared with the prior art, the present disclosure has the following beneficial effects:

1) The combined detection of gene point mutation and methylation is realized in the present disclosure, and two kinds of templates are needed according to different types of the site mutation to be detected, thereby reducing the demand for samples, experimental operation steps and detection cycle.

2) The detection reaction procedure is ingeniously designed in the present disclosure, ensuring the stability and detection limit of the detection system, and avoiding false positives caused by amplification of wild type templates.

3) The combined detection of point mutation and methylation of driver gene is ingeniously used in the present disclosure, evaluating the negative and positive of samples from two dimensions, and improving the specificity and sensitivity of detection.

DETAILED DESCRIPTION OF THE EMBODIMENTS

Example 1 Preparation of the Combined Auxiliary Diagnostic Kit of Gene Point Mutation and Methylation of the Bladder Cancer Driver Genes

```
1. Design of primers and probes
1) Point mutation targets, primers and probes of driver genes
FGFR3 exon7
                                          (SEQ ID NO: 1)
GTGCTGGGTGAGGGCCCTGGGGCGGCGCGGGGGTGGGGGCGGCAGTGG

CGGTGGTGGTGAGGGAGGGGGTGGCCCCTGAGCGTCATCTGCCCCCACAGAG

CGCT[C]CCCGCACCGGCCCATCCTGCAGGCGGGGCTGCCGGCCAACCAGACG

GCGGTGCTGGGCAGCGACGTGGAGTTCCACTGCAAGGTGTACAGTGACGCAC

AGCCCCACATCCAGTGGCTCAAGCACGTGGA c.746C>G
After heavy salt transformation:
GTGTTGGGTGAGGGTTTTGGGGCGGCGCGGGGGTGGGGGCGGTAGTGG

CGGTGGTGGTGAGGGAGGGGGTGGTTTTTGAGCGTTATTTGTTTTTATAGAGC

GTTMTTCGTATCGGTTTATTTTGTAGGCGGGGTTGTCGGTTAATTAGACGGCG

GTGTTGGGTAGCGACGTGGAGTTTTATTGTAAGGTGTATAGTGACGTATAGTTT

TATATTTAGTGGTTTAAGTACGTGGA

FGFR3-ARMS-F1:
                                          (SEQ ID NO: 7)
GAGCGTTATTTGTTTTTATAGAGCGTTG

FGFR3-ARMS-F2:
                                          (SEQ ID NO: 8)
TTGAGCGTTATTTGTTTTTATAGAGCGTTGT

FGFR3-ARMS-F3:
                                          (SEQ ID NO: 9)
GAGCGTTATTTGTTTTTATAGAGCGTTGTT

FGFR3-ARMS-F4:
                                          (SEQ ID NO: 10)
GAGCGTTATTTGTTTTTATAGAGCGGTG

FGFR3-ARMS-R:
                                          (SEQ ID NO: 11)
TAAAACTATACGTCACTATACACCTTAC

FGFR3-ARMS-FAM:
                                          (SEQ ID NO: 12)
CGTATCGGTTTATTTTGTAGGCGGGGTTGTCG
```

-continued

TERT promoter (SEQ ID NO: 2)

GCTTCCCACGTGCGCAGCAGGACGCAGCGCTGCCTGAAACTCGCGCCGC

GAGGAGAGGGCGGGGCCGCGGAAAGGAAGGGGAGGGGCTGGGAGGGCCCG

GAGGGGGCTGGGCCGGGGACCCGG[G]AGGGGTCGGGACGGGGCGGGGTCCG

CGCGGAGGAGGCGGAGCTGGAAGGTGAAGGGGCAGGACGGGTGCCCGGGTC

CCCAGTCCCTCCGCCACGTGGGAAG c.1-146C>T
After heavy salt transformation:
GTTTTTTACGTGCGTAGTAGGACGTAGCGTTGTTTGAAATTCGCGTCGCG

AGGAGAGGGCGGGGTCGCGGAAAGGAAGGGGAGGGGTTGGGAGGGTTCGGA

GGGGGTTGGGTCGGGGATTCGG[G]AGGGGTCGGGACGGGGCGGGGTTCGCGC

GGAGGAGGCGGAGTTGGAAGGTGAAGGGGTAGGACGGGTGTTCGGGTTTTTA

GTTTTTTCGTTACGTGGGAAG

TERT-ARMS-F1:

(SEQ ID NO: 13)

GAGGGGGTTGGGTCGGGGATTCGGA

TERT-ARMS-F2:

(SEQ ID NO: 14)

GGGTTGGGTCGGGGATTCGGAA

TERT-ARMS-F3:

(SEQ ID NO: 15)

GGTTGGGTCGGGGATTCGGAAG

TERT-ARMS-F4:

(SEQ ID NO: 16)

GAGGGGGTTGGGTCGGGGATTCTGA

TERT-ARMS-R:

(SEQ ID NO: 17)

CCGAACACCCGTCCTACCCCTTCA

TERT-ARMS-HEX:

(SEQ ID NO: 18)

TCGGGACGGGGCGGGGTTCGCG

PLEKHS1

(SEQ ID NO: 3)

GAGCACTGGACCAGCGACCTCTTGGCTTCCAGTAAGTACTGCTTGGTGTA

TCTGGTTTGGACTTCCAAGGCTGGGATGATCTAGAAGCTTTTTTGCAATT[G]AA

CAATTGCAAAATTGGAAATGGAAAATTTTGCAGATATGCTGTATTTCTGTTATGG

GCACTTTCTTCATAAGCTTCCTAGGCTATACTATAGTCAGAGGGAA

After heavy salt transformation:
GAGTATTGGATTAGCGATTTTTTGGTTTTTAGTAAGTATTGTTTGGTGTATT

TGGTTTGGATTTTTAAGGTTGGGATGATTTAGAAGTTTTTTTGTAATT[G]AATAA

TTGTAAAATTGGAAATGGAAAATTTTGTAGATATGTTGTATTTTTGTTATGGGTA

TTTTTTTTATAAGTTTTTTAGGTTATATTATAGTTAGAGGGAA

G>A
PLEKHS1-ARMS-F1:

(SEQ ID NO: 19)

GATGATTTAGAAGTTTTTTTGTAATTA

PLEKHS1-ARMS-F2:

(SEQ ID NO: 20)

GATGATTTAGAAGTTTTTTTGTAATTAA

PLEKHS1-ARMS-F3:

(SEQ ID NO: 21)

GGATGATTTAGAAGTTTTTTTGTAATTAAA

-continued

PLEKHS1-ARMS-F4:

(SEQ ID NO: 22)

GATGATTTAGAAGTTTTTTTGTAAGTA

PLEKHS1-ARMS-R:

(SEQ ID NO: 23)

CTTATAAAAAAAATACCCATAACAAAAATAC

PLEKHS1-ARMS-ROX:

(SEQ ID NO: 24)

TAAAATTGGAAATGGAAAATTTTGTAGATATG

2) Driver gene methylation templates, primers and probes
>OTX1
Methylation site template:

(SEQ ID NO: 4)

CGTTTGGAGGTTTTTTGATTTGTTTTTATATTTAATTTTGTGTAAATTTTTTA

TTTCGTTTGTCGGGGTGGGGGAGTGGGGGAGATTAGAAATAAGGGGTAGAAAT

TTTT[CG]AAAGGGAATAAAGTGTTTAATTTTTAGGAGGAGGTGTTATTTAAAAG

ATT[CG]TTTAGTTTAGAGTTGGTTT[CG]GGTGGGAAATGGGTTT[CG]TT[CG]TA

CG+AATAATT[CG]GGGAAAT[CG]TTTTAAGGAGGATTTTTA[CG]TAGTATGTGGA

AAAAAGTTGAGGGTAGGGGTTTGTGGTTATATTTTTTATTAAAAAGTTTTTGTT

AGAGGTAGTTTAAGAAAGAGAGAGAAAGAGCGAAAAAGAAATTTTT

OTX1-bis-ARMS-F1:

(SEQ ID NO: 25)

CGTTTAGTTTAGAGTTGGTTTCG

OTX1-bis-ARMS-F2:

(SEQ ID NO: 26)

AGTTTAGAGTTGGTTTCGGG

OTX1-bis-ARMS-R1:

(SEQ ID NO: 27)

CTACGTAAAAATCCTCCTTAAAACG

OTX1-bis-ARMS-R2:

(SEQ ID NO: 28)

CTACGTAAAAATCCTCCTTAAAAC

OTX1-bis-ARMS-R3:

(SEQ ID NO: 29)

CTACGTAAAAATCCTCCTTAAATCG

OTX1-bis-ARMS-FAM:

(SEQ ID NO: 30)

ATGGGTTTCGTTCGTACGAATAA

>NID2

(SEQ ID NO: 5)

GTAGTGGTTATTATATTTGGTTTTCGTTAATTTTTTTAAGGTAGCGGTCGTT

GGAGTAGCGGGGTTGGCGGGGTAAAAGTTTTTGGTTAGGGTTGTTTGGAGTTG

TTTTTTTTATTT[CG]TTTTTAGGGAGTTTT[CG]GGTTATTTTTTTATT[CG]GGTTG

TTT[CG][CG]GTTTTTAAGGAGTTTTATTTT[CG]GGATTAAATGGTT[CG]TAAGGT

TTGGGGTAG[CG]G[CG]TTGTAGGAGATGAGTTTAG[CG]TAAAGGGAATTT[CG]

TAGCGGCGAGTGCGGTTGTTGGTTTGCGCGTTGTGGTTTTAATAGGTTGGTAGG

GCGCGGGCGGGTGGCGGGGTTGCGGTATGAGTTTTGTTTTTTGTTTTG

NID2-bis-ARMS-F1:

(SEQ ID NO: 31)

GGTTAGGGTTGTTTGGAGTTGT

NID2-bis-ARMS-R1:

(SEQ ID NO: 32)

CAAACCTTACGAACCATTTAATCCC

NID2-bis-ARMS-R2:

(SEQ ID NO: 33)

CAAACCTTACGAACCATTTAATACC

-continued

NID2-bis-ARMS-R3:

(SEQ ID NO: 34)

CAAACCTTACGAACCATTTAATCAC

NID2-bis-ARMS-HEX:

(SEQ ID NO: 35)

CGGGTTGTTTCGCGCGGTTTTTAAGGAG

NRN1

(SEQ ID NO: 6)

TCGGGAGGATCGGATATTTTAATTTTTCGGTTTTTAACGCGGGCGTTTGTT

CGCGAGCGTCGGGTTAGACGTCGAAGAGGAAGGTGATCGAATTCGTAGTAGTT

TTCGAGAGCGTATTCGTTTGTAAATTGTTGTAGGAAGAG+CQAGG[CG]GGTTT

TG[CG]TTTTTTAATT[CG]GAA[CG]GGAAGTATTGGGGAAGGGAT[CG]AGGTTA

ATTT[CG]ATTTT[CG]TTGGGGTAGATA[CG]TAAATTTTTTTAAATTTT[CG]AGTT

TATTT TATAG[CG]AATATTAAATATTTTTG[CG]ATTATAATATTAATAAATCGAATA

TTGA[CG]TAAAATTTTAAGAATAAACGAATTTTT

NRN1-bis-ARMS-F1:

(SEQ ID NO: 36)

GTTTGTAAATTGTTGTAGGAAGCGC

NRN1-bis-ARMS-ROX:

(SEQ ID NO: 37)

ATCGAAATTAACCTCGATCCCTTCC

NRN1-bis-ARMS-R2:

(SEQ ID NO: 38)

ATATTCGCTATAAAATAAACCCG

NRN1-bis-ARMS-R3:

(SEQ ID NO: 39)

CGTTTATTCTTAAAATTTTCCG

NRN1-bis-ARMS-R1:

(SEQ ID NO: 40)

ATAATCGCAAAAATATTTAATATCCG

The above [ ] area was the detection site.
3) ATCB gene primers and probes
ATCB-BIS-F2:

(SEQ ID NO: 41)

AGTGAGAAAGGGTGTAGTTTTGGGAG

ATCB-BIS-R3:

(SEQ ID NO: 42)

CCACAAAAAAATAACCCAAATAAATAACCCACT

ATCB-VIC:

(SEQ ID NO: 43)

CCTCTTCTAATAACCACCTCCCTCCTTCCTAAC

2. Preparation and Composition of Kit

The main components of the urine bladder cancer driver gene point mutation methylation combined detection kit of the present disclosure comprises the following components:

| reagent name | main components |
| --- | --- |
| primer & probe A | mixture of three driver gene point mutations, internal reference primer and probe |
| primer & probe B | mixture of three driver gene methylation, internal reference primer and probe |
| Gold 360 Master Mix | DNA polymerase, Mg²⁺, dN(15)TPs, |
| PCR enhancer | DTT and BSA |
| point mutation positive quality control | adenovirus packaging positive mutant plasmid |
| methylation positive quality control | methylation-positive nucleic acid after methylase transformation |

| reagent name | main components |
| --- | --- |
| negative control | T cells after wild-type plasmid transfection |
| NF-H₂O | nuclease-free water |

Primer & probe A: The primers and probes of FGFR3\TERT\ PLEKHS1\ATCB were mixed in a proper proportion to prepare primer & probe A.

Primer & probe B: The methylation detection primers and probes of OTX1\NRN1\NID2\ATCB were mixed in a proper proportion to prepare primer & probe B.

3. Reaction System and Detection Procedure of the Kit

The same sample was detected for point mutation and methylation respectively. That is, part of the nucleic acid in the same sample was carried out for heavy salt transformation according to the instructions of heavy salt transformation reagent (EZ DNA Methylation-Gold, Cat D5005), and part of nucleic acid was used for gene point mutation detection. Sample detection system was prepared as shown in the table below:

Gene point mutation detection reaction system (reaction tube A):

| reagent name | reaction volume (μL) |
|---|---|
| Primer&Probe A | 2 |
| Hotstart HiTaq DNA polymerase | 1 |
| Hotstart HiTaq Buffer | 24 |
| PCR enhancer | 1 |
| nucleic acid to be detected | 5 |
| NF-H$_2$O | 17 |
| total volume | 50 |

Gene methylation detection reaction system (reaction tube B):

| reagent name | the reaction volume (μL) |
|---|---|
| Primer&Probe B | 2 |
| Hotstart HiTaq DNA polymerase | 1 |
| Hotstart HiTaq Buffer | 24 |

-continued

| reagent name | the reaction volume (μL) |
|---|---|
| PCR enhancer | 1 |
| purified nucleic acid after heavy salt transformation | 5 |
| NF-H$_2$O | 17 |
| total volume | 50 |

The reaction system for the sample to be detected was prepared according to the above table, the reaction system was mixed uniformly by vortex, the reaction system after mixing was placed on a thermal cycler and was detected according to the following procedure:

| the first stage | 95° C. | 10 min | 1 cycle | pre-denaturation |
|---|---|---|---|---|
| the second stage | 95° C. | 15 s | 15 cycles | high TM template |
| | 59° C. | 45 s | | enrichment |
| | 72° C. | 1 min | | |
| the third stage | 95° C. | 15 s | 35 cycles | |
| | 55° C. | 45 s | | |
| | 72° C. | 1 min | | collection of the fluorescence signal |
| the fourth stage | 40° C. | 1 min | 1 cycle | cooling |

4. Standards for Determination of Negative and Positive Results

The negative and positive was interpreted according to the following table:

| detection category | gene name | standard for positive results | standard for negative results | standards for determination of positive results | standards for determination of negative results |
|---|---|---|---|---|---|
| point mutation detection | FGFR3 | Ct < 30.5 | Ct > 30.5 or no CT value | The results of point mutation test and methylation test are at least 1 positive, and the sample is interpreted as positive. | The results of point mutation test and methylation test are both negative, the sample is interpreted as negative. |
| | TERT | Ct < 28.5 | Ct > 28.5 or no CT value | | |
| | PLEKHS1 | Ct < 30.5 | Ct > 30.5 or no CT value | | |
| | ATCB | Ct < 36 | Ct < 36 | | |
| methylation detection | OTX1 | Ct < 30.5 | Ct > 30.5 or no CT value | | |
| | NRN1 | Ct < 28.5 | Ct > 28.5 or no CT value | | |
| | NID2 | Ct < 30.5 | Ct > 30.5 or no CT value | | |
| | ATCB | Ct < 36 | Ct < 36 | | |

Example 2 Optimization of Primers and Probes of
the Combined Auxiliary Diagnostic Kit of Gene
Point Mutation and Methylation of the Bladder
Cancer Driver Genes The primers and probes combination and primer concentration for point mutation was screened and optimized according to the following table:

| gene | primers and probes combination | forward primer concentration gradient(μM) | reverse primer concentration gradient (μM) | probes concentration gradient(μM) |
|---|---|---|---|---|
| FGFR3 | FGFR3-ARMS-F1; FGFR3-ARMS-R; FGFR3-ARMS-FAM; | 2.5/5/10/25/40/50 | 2.5/5/10/25/40/50 | 2.5/5/10/25/40 |
| | FGFR3-ARMS-F2; FGFR3-ARMS-R; FGFR3-ARMS-FAM; | 2.5/5/10/25/40/50 | 2.5/5/10/25/40/50 | 2.5/5/10/25/40 |
| | FGFR3-ARMS-F3; FGFR3-ARMS-R; FGFR3-ARMS-FAM; | 2.5/5/10/25/40/50 | 2.5/5/10/25/40/50 | 2.5/5/10/25/40 |
| | FGFR3-ARMS-F4 FGFR3-ARMS-R; FGFR3-ARMS-FAM; | 2.5/5/10/25/40/50 | 2.5/5/10/25/40/50 | 2.5/5/10/25/40 |
| TERT | TERT-ARMS-F1; TERT-ARMS-R; TERT-ARMS-HEX; | 2.5/5/10/25/40/50 | 2.5/5/10/25/40/50 | 2.5/5/10/25/40 |
| | TERT-ARMS-F2; TERT-ARMS-R; TERT-ARMS-HEX; | 2.5/5/10/25/40/50 | 2.5/5/10/25/40/50 | 2.5/5/10/25/40 |
| | TERT-ARMS-F3; TERT-ARMS-R; TERT-ARMS-HEX; | 2.5/5/10/25/40/50 | 2.5/5/10/25/40/50 | 2.5/5/10/25/40 |
| | TERT-ARMS-F4; TERT-ARMS-R; TERT-ARMS-HEX; | 2.5/5/10/25/40/50 | 2.5/5/10/25/40/50 | 2.5/5/10/25/40 |
| PLEKHS1 | PLEKHS1-ARMS-F1; PLEKHS1-ARMS-R; PLEKHS1-ARMS-ROX; | 2.5/5/10/25/40/50 | 2.5/5/10/25/40/50 | 2.5/5/10/25/40 |
| | PLEKHS1-ARMS-F2; PLEKHS1-ARMS-R; PLEKHS1-ARMS-ROX; | 2.5/5/10/25/40/50 | 2.5/5/10/25/40/50 | 2.5/5/10/25/40 |
| | PLEKHS1-ARMS-F3; PLEKHS1-ARMS-R; PLEKHS1-ARMS-ROX; | 2.5/5/10/25/40/50 | 2.5/5/10/25/40/50 | 2.5/5/10/25/40 |
| | PLEKHS1-ARMS-F4; PLEKHS1-ARMS-R; PLEKHS1-ARMS-ROX; | 2.5/5/10/25/40/50 | 2.5/5/10/25/40/50 | 2.5/5/10/25/40 |
| ATCB | ATCB-ARMS-F; ATCB-ARMS-R; ATCB-ARMS-VIC; | 2.5/5/10/25/40/50 | 2.5/5/10/25/40/50 | 2.5/5/10/25/40 |

The primers and probes combination and the concentration of primers and probes for methylation was screened and optimized according to the following table:

| gene | primers and probes combination | forward primer concentration gradient(μM) | reverse primer concentration gradient (μM) | probes concentration gradient(μM) |
|---|---|---|---|---|
| OTX1 | OTX1-BIS-F1; OTX1-BIS-R1; OTX1-BIS-FAM; | 2.5/5/10/25/40/50 | 2.5/5/10/25/40/50 | 2.5/5/10/25/40 |
| | OTX1-BIS-F2; OTX1-BIS-R1; OTX1-BIS-FAM; | 2.5/5/10/25/40/50 | 2.5/5/10/25/40/50 | 2.5/5/10/25/40 |
| | OTX1-BIS-F1; OTX1-BIS-R2; OTX1-BIS-FAM; | 2.5/5/10/25/40/50 | 2.5/5/10/25/40/50 | 2.5/5/10/25/40 |
| | OTX1-BIS-F2; OTX1-BIS-R2; OTX1-BIS-FAM; | 2.5/5/10/25/40/50 | 2.5/5/10/25/40/50 | 2.5/5/10/25/40 |
| | OTX1-BIS-F1; OTX1-BIS-R3; OTX1-BIS-FAM; | 2.5/5/10/25/40/50 | 2.5/5/10/25/40/50 | 2.5/5/10/25/40 |

-continued

| gene | primers and probes combination | forward primer concentration gradient(μM) | reverse primer concentration gradient (μM) | probes concentration gradient(μM) |
|---|---|---|---|---|
|  | OTX1-BIS-F2; OTX1-BIS-R3; OTX1-BIS-FAM; | 2.5/5/10/25/40/50 | 2.5/5/10/25/40/50 | 2.5/5/10/25/40 |
| NRN1 | NRN1-BIS-F1; NRN1-BIS-R1; NRN1-BIS-HEX; | 2.5/5/10/25/40/50 | 2.5/5/10/25/40/50 | 2.5/5/10/25/40 |
|  | NRN1-BIS-F1; NRN1-BIS-R2; NRN1-BIS-HEX; | 2.5/5/10/25/40/50 | 2.5/5/10/25/40/50 | 2.5/5/10/25/40 |
|  | NRN1-BIS-F1; NRN1-BIS-R3; NRN1-BIS-HEX; | 2.5/5/10/25/40/50 | 2.5/5/10/25/40/50 | 2.5/5/10/25/40 |
| NID2 | NID2-BIS-F1 NID2-BIS-R1 NID2-BIS-ROX; | 2.5/5/10/25/40/50 | 2.5/5/10/25/40/50 | 2.5/5/10/25/40 |
|  | NID2-BIS-F1; NID2-BIS-R2; NID2-BIS-ROX; | 2.5/5/10/25/40/50 | 2.5/5/10/25/40/50 | 2.5/5/10/25/40 |
|  | NID2-BIS-F1; NID2-BIS-R3; NID2-BIS-ROX; | 2.5/5/10/25/40/50 | 2.5/5/10/25/40/50 | 2.5/5/10/25/40 |
| ATCB | ATCB-BIS-F; ATCB-BIS-R; ATCB-BIS-VIC; | 2.5/5/10/25/40/50 | 2.5/5/10/25/40/50 | 2.5/5/10/25/40 |

According to Example 1, the reaction system was formulated, and the point mutation positive quality control product, methylation positive quality control product and negative control product were used as system test templates, and the primers and probes combination and concentration in the above table were tested respectively.

Test Result

Specific test results of primers and probes combination:

| gene | primers and probes combination | forward/ reverse primer amount (μM) | probe amount (μM) | point mutation positive quality control product (Ct) | negative control product (Whether there is a non-specific amplification curve) |
|---|---|---|---|---|---|
| FGFR3 | FGFR3-ARMS-F1; FGFR3-ARMS-R; FGFR3-ARMS-FAM; | 10 | 5 | 22.4 | None |
|  | FGFR3-ARMS-F2; FGFR3-ARMS-R; FGFR3-ARMS-FAM; | 10 | 5 | 22.8 | Yes |
|  | FGFR3-ARMS-F3; FGFR3-ARMS-R; FGFR3-ARMS-FAM; | 10 | 5 | 23.3 | Yes |
|  | FGFR3-ARMS-F4; FGFR3-ARMS-R; FGFR3-ARMS-FAM; | 10 | 5 | 21.3 | None |
| TERT | TERT-ARMS-F1; TERT-ARMS-R; TERT-ARMS-HEX; | 10 | 5 | 25.7 | None |
|  | TERT-ARMS-F2; TERT-ARMS-R; TERT-ARMS-HEX; | 10 | 5 | 26.5 | None |
|  | TERT-ARMS-F3; TERT-ARMS-R; TERT-ARMS-HEX; | 10 | 5 | 22.6 | Yes |
|  | TERT-ARMS-F4; TERT-ARMS-R; TERT-ARMS-HEX; | 10 | 5 | 24.3 | None |

-continued

| gene | primers and probes combination | forward/reverse primer amount (μM) | probe amount (μM) | methylation positive quality control product (Ct) | negative control product (existence of a non-specific amplification curve: Yes or None) |
|---|---|---|---|---|---|
| PLEKHS1 | PLEKHS1-ARMS-F1; PLEKHS1-ARMS-R; PLEKHS1-ARMS-ROX; | 10 | 5 | 21.5 | Yes |
| | PLEKHS1-ARMS-F2; PLEKHS1-ARMS-R; PLEKHS1-ARMS-ROX; | 10 | 5 | 22.9 | None |
| | PLEKHS1-ARMS-F3; PLEKHS1-ARMS-R; PLEKHS1-ARMS-ROX; | 10 | 5 | 23.4 | Yes |
| | PLEKHS1-ARMS-F4; PLEKHS1-ARMS-R; PLEKHS1-ARMS-ROX; | 10 | 5 | 21.8 | None |
| ATCB | ATCB-ARMS-F; ATCB-ARMS-R; ATCB-ARMS-VIC; | 10 | 5 | 19.8 | None |

| gene | primers and probes combination | forward/reverse primer amount (μM) | probe amount (μM) | methylation positive quality control product (Ct) | negative control product (existence of a non-specific amplification curve: Yes or None) |
|---|---|---|---|---|---|
| OTX1 | OTX1-BIS-F1; OTX1-BIS-R1; OTX1-BIS-FAM; | 10 | 5 | 22.3 | None |
| | OTX1-BIS-F2; OTX1-BIS-R1; OTX1-BIS-FAM; | 10 | 5 | 24.5 | Yes |
| | OTX1-BIS-F1; OTX1-BIS-R2; OTX1-BIS-FAM; | 10 | 5 | 21.8 | Yes |
| | OTX1-BIS-F2; OTX1-BIS-R2; OTX1-BIS-FAM; | 10 | 5 | 23.4 | None |
| | OTX1-BIS-F1; OTX1-BIS-R3; OTX1-BIS-FAM; | 10 | 5 | 22.9 | None |
| | OTX1-BIS-F2; OTX1-BIS-R3; OTX1-BIS-FAM; | 10 | 5 | 23.9 | None |
| NRN1 | NRN1-BIS-F1; NRN1-BIS-R1; NRN1-BIS-HEX | 10 | 5 | 21.3 | Yes |
| | NRN1-BIS-F1; NRN1-BIS-R2; NRN1-BIS-HEX; | 10 | 5 | 24.7 | None |
| | NRN1-BIS-F1; NRN1-BIS-R3; NRN1-BIS-HEX; | 10 | 5 | 25.8 | Yes |
| NID2 | NID2-BIS-F1; NID2-BIS-R1; NID2-BIS-ROX; | 10 | 5 | 22.7 | Yes |
| | NID2-BIS-F1; NID2-BIS-R2; NID2-BIS-ROX; | 10 | 5 | 21.6 | None |
| | NID2-BIS-F1; NID2-BIS-R3; NID2-BIS-ROX; | 10 | 5 | 20.6 | None |
| ATCB | ATCB-BIS-F; ATCB-BIS-R; ATCB-BIS-VIC; | 10 | 5 | 19.6 | None |

Comparison table of primers and probes concentration gradient test results:

| gene | primers and probes combination | forward primer concentration gradient(μM) | reverse primer concentration gradient(μM) | probes concentration gradient(μM) | point mutation positive quality control products with different primer concentrations (Ct) | negative control product (existence of non-specific products: Yes or None) |
|---|---|---|---|---|---|---|
| FGFR3 | FGFR3-ARMS-F1; FGFR3-ARMS-R; FGFR3-ARMS-FAM; | 2.5/5/10/ 25/40/50 | 2.5/5/10/ 25/40/50 | 10 | 2.5: 24.8 5: 22.4 10: 21.9 25: 21.5 40: 21.2 50: 20.8 | Yes, at 40/50 μM |
| | FGFR3-ARMS-F2; FGFR3-ARMS-R; FGFR3-ARMS-FAM; | 2.5/5/10/ 25/40/50 | 2.5/5/10/ 25/40/50 | 10 | 2.5: 23.9 5: 22.8 10: 22.02 25: 21.8 40: 20.8 50: 20.5 | Yes, at 50 μM |
| | FGFR3-ARMS-F3; FGFR3-ARMS-R; FGFR3-ARMS-FAM; | 2.5/5/10/ 25/40/50 | 2.5/5/10/ 25/40/50 | 10 | 2.5: 24.8 5: 23.3 10: 22.15 25: 21.8 40: 21.5 50: 21.6 | Yes, at 40/50 μM |
| | FGFR3-ARMS-F4; FGFR3-ARMS-R; FGFR3-ARMS-FAM; | 2.5/5/10/ 25/40/50 | 2.5/5/10/ 25/40/50 | 10 | 2.5: 5: 21.3 10: 20.8 25: 19.8 40: 20.5 50: 19.7 | None |
| TERT | TERT-ARMS-F1; TERT-ARMS-R; TERT-ARMS-HEX; | 2.5/5/10/ 25/40/50 | 2.5/5/10/ 25/40/50 | 10 | 2.5: 28.7 5: 25.7 10: 24.8 25: 24.5 40: 23.8 50: 22.9 | Yes, at 10/25/40/50 μM |
| | TERT-ARMS-F2; TERT-ARMS-R; TERT-ARMS-HEX; | 2.5/5/10/ 25/40/50 | 2.5/5/10/ 25/40/50 | 10 | 2.5: 28.9 5: 26.5 10: 25.9 25: 25.1 40: 24.9 50: 24.5 | Yes, at 25/40/50 μM |
| | TERT-ARMS-F3; TERT-ARMS-R; TERT-ARMS-HEX; | 2.5/5/10/ 25/40/50 | 2.5/5/10/ 25/40/50 | 10 | 2.5: 24.8 5: 22.6 10: 21.8 25: 21.5 40: 20.8 50: 19.8 | Yes, at 25/40/50 μM |
| | TERT-ARMS-F4; TERT-ARMS-R; TERT-ARMS-HEX; | 2.5/5/10/ 25/40/50 | 2.5/5/10/ 25/40/50 | 10 | 2.5: 26.9 5: 24.3 10: 23.8 25: 23.5 40: 22.5 50: 22.0 | Yes, at 50 μm |
| PLEK HS1 | PLEKHS1-ARMS-F1 PLEKHS1-ARMS-R; PLEKHS1-ARMS-ROX; | 2.5/5/10/ 25/40/50 | 2.5/5/10/ 25/40/50 | 10 | 2.5: 23.8 5: 21.5 10: 20.5 25: 20.0 40: 19.5 50: 19.5 | Yes, at 25/40/50 μM |
| | PLEKHS1-ARMS-F2 PLEKHS1-ARMS-R; PLEKHS1-ARMS-ROX; | 2.5/5/10/ 25/40/50 | 2.5/5/10/ 25/40/50 | 10 | 2.5: 25.5 5: 22.9 10: 22.5 25: 20.5 40: 20.1 50: 19.5 | Yes, at 25/40/50 μM |
| | PLEKHS1-ARMS-F3 PLEKHS1-ARMS-R; PLEKHS1-ARMS-ROX; | 2.5/5/10/ 25/40/50 | 2.5/5/10/ 25/40/50 | 10 | 2.5: 24.5 5: 23.4 10: 22.5 25: 22.6 40: 21.8 50: 21.5 | Yes, at 40/50 μM |

-continued

| | PLEKHS1-ARMS-F4 PLEKHS1-ARMS-R; PLEKHS1-ARMS-ROX; | 2.5/5/10/ 25/40/50 | 2.5/5/10/ 25/40/50 | 10 | 2.5: 24.0 5: 21.8 10: 21.0 25: 20.5 40: 20.0 50: 19.5 | None |
| ATCB | ATCB-ARMS-F; ATCB-ARMS-R; ATCB-ARMS-VIC; | 2.5/5/10/ 25/40/50 | 2.5/5/10/ 25/40/50 | 10 | 2.5: 21.5 5: 19.8 10: 19.5 25: 19.0 40: 18.5 50: 18.0 | None |

| gene | primers and probes combination | Forward/ reverse primer concentration gradient(µM) | probes concentration (µM) | Methylation positive quality control products with different primer concentrations (Ct) | negative control product (existence of a non-specific amplification curve: Yes or None) |
|---|---|---|---|---|---|
| OTX1 | OTX1-BIS-F1; OTX1-BIS-R1 OTX1-BIS-FAM; | 2.5/5/10/ 25/40/50 | 10 | 2.5: 25.9 5: 22.3 10: 21.8 25: 21.5 40: 21.0 50: 21.0 | Yes, at 25/40/50 µM |
| | OTX1-BIS-F2; OTX1-BIS-R1; OTX1-BIS-FAM; | 2.5/5/10/ 25/40/50 | 10 | 2.5: 25.5 5: 24.5 10: 23.5 25: 23.2 40: 22.8 50: 22.5 | Yes, at 25/40/50 µM |
| | OTX1-BIS-F1; OTX1-BIS-R2; OTX1-BIS-FAM; | 2.5/5/10/ 25/40/50 | 10 | 2.5: 23.6 5: 21.8 10: 21.5 25: 20.6 40: 20.1 50: 20.3 | Yes, at 40/50 µM |
| | OTX1-BIS-F2; OTX1-BIS-R2; OTX1-BIS-FAM; | 2.5/5/10/ 25/40/50 | 10 | 2.5: 25.4 5: 23.4 10: 22.8 25: 22.0 40: 21.5 50: 21.0 | Yes, at 450 µM |
| | OTX1-BIS-F1; OTX1-BIS-R3; OTX1-BIS-FAM; | 2.5/5/10/ 25/40/50 | 10 | 2.5: 23.5 5: 22.9 10: 21.0 25: 20.5 40: 20.0 50: 19.5 | None |
| | OTX1-BIS-F2; OTX1-BIS-R3; OTX1-BIS-FAM; | 2.5/5/10/ 25/40/50 | 10 | 2.5: 25.5 5: 23.9 10: 22.5 25: 22.0 40: 21.5 50: 21.0 | Yes, at 40/50 µM |
| NRN1 | NRN1-BIS-F1; NRN1-BIS-R1; NRN1-BIS-HEX; | 2.5/5/10/ 25/40/50 | 10 | 2.5: 23.5 5: 21.3 10: 20.5 25: 20.0 40: 19.5 50: 19.0 | Yes, at 40/50 µM |
| | NRN1-BIS-F1; NRN1-BIS-R2; NRN1-BIS-HEX; | 2.5/5/10/ 25/40/50 | 10 | 2.5: 25.8 5: 24.7 10: 22.5 25: 22.2 40: 22.0 50: 21.8 | Yes, at 40/50 µM |
| | NRN1-BIS-F1; NRN1-BIS-R3; NRN1-BIS-HEX; | 2.5/5/10/ 25/40/50 | 10 | 2.5: 26.8 5: 25.8 10: 24.3 25: 23.5 40: 23.0 50: 22.5 | None |

-continued

| NID2 | NID2-BIS-F1;<br>NID2-BIS-R1;<br>NID2-BIS-ROX; | 2.5/5/10/<br>25/40/50 | 10 | 2.5: 24.8<br>5: 22.7<br>10: 21.5<br>25: 21.0<br>40: 20.5<br>50: 20.0 | Yes, at<br>25/40/50 μM |
|  | NID2-BIS-F1;<br>NID2-BIS-R2;<br>NID2-BIS-ROX; | 2.5/5/10/<br>25/40/50 | 10 | 2.5: 23.5<br>5: 21.6<br>10: 21.0<br>25: 20.5<br>40: 20.0<br>50: 20.3 | Yes, at<br>25/40/50 μM |
|  | NID2-BIS-F1;<br>NID2-BIS-R3;<br>NID2-BIS-ROX; | 2.5/5/10/<br>25/40/50 | 10 | 2.5: 23.5<br>5: 20.6<br>10: 20.3<br>25: 19.5<br>40: 19.0<br>50: 18.9 | None |
| ATCB | ATCB-BIS-F;<br>ATCB-BIS-R;<br>ATCB-BIS-VIC; | 2.5/5/10/<br>25/40/50 | 10 | 2.5: 21.5<br>5: 19.6<br>10: 19.5<br>25: 19.0<br>40: 18.5<br>50: 18.0 | None |

According to the comprehensive evaluation of primer specificity and amplification efficiency, the optimal primers and probes combination and concentration were shown in the following table:

|  | Gene | primers and probes combination | the amount of primers and probes(μM) |
|---|---|---|---|
| Primer&<br>Probe A | FGFR3 | FGFR3-ARMS-F4:<br>FGFR3-ARMS-R;<br>FGFR3-ARMS-FAM; | 25, 25, 15 |
|  | TERT | TERT-ARMS-F4;<br>TERT-ARMS-R:<br>TERT-ARMS-HEX; | 25, 25, 10 |
|  | PLEKHS1 | PLEKHS1-ARMS-F4;<br>PLEKHS1-ARMS-R;<br>PLEKHS1-ARMS-ROX; | 25, 25, 10 |
|  | ATCB | ATCB-ARMS-F;<br>ATCB-ARMS-R;<br>ATCB-ARMS-VIC: | 2.5, 2.5, 5 |
| Primer&<br>Probe B | OTX1 | OTX1-BIS-F1;<br>OTX1-BIS-R3;<br>OTX1-BIS-FAM; | 25, 25.15 |
|  | NRN1 | NRN1-BIS-F1;<br>NRN1-BIS-R2;<br>NRN1-BIS-HEX; | 25, 25, 15 |
|  | NID2 | NID2-BIS-F1;<br>NID2-BIS-R3;<br>NID2-BIS-ROX; | 25, 25, 15 |
|  | ATCB | ATCB-BIS-F;<br>ATCB-BIS-R;<br>ATCB-BIS-VIC; | 2.5, 2.5, 5 |

Example 3 Optimization of Reactive Enzymes and Detection Procedures of the Combined Auxiliary Diagnostic Kit of Gene Point Mutation and Methylation of the Bladder Cancer Driver Genes Point mutation positive quality control products, methylation positive quality control products and negative quality control products were used as detection templates (10 replicates).

The optimization test of reactive enzymes and the detection procedures are respectively carried out according to the following table:

| test point | types of enzymes | enzyme dosage (U) | statistical method |
|---|---|---|---|
| reactive enzymes | Taq DNA polymerase, HiFi Master Mix, Gold 360 Master Mix, 2 G Robust Master Mix | 1-100 | The detection rate of positive samples, Ct value and false negative number of negative samples were counted. |

| test point | test type | result statistics |
|---|---|---|
| detection procedures | standard qPCR detection procedure the detection procedure of the present disclosure | The detection rate of positive samples, Ct value and false negative number of negative samples were counted |

The standard qPCR detection procedure was consisted of the first stage, the third stage and the fourth stage in Example 1.

Test Results

| DNA polymerase | detection rate of point mutation positive quality control products | average Ct values of point mutation positive quality control products | detection rate of methylation positive quality control products | average Ct values of methylated positive quality control products | false negative number of negative control products |
|---|---|---|---|---|---|
| Taq DNA polymerase | 75% | 32.05 | 95% | 26.5 | 4 |
| HiFi Master Mix | 100% | 29.05 | 90% | 25.5 | 3 |
| Gold 360 Master Mix | 100% | 28.5 | 100% | 29.5 | 0 |
| 2 G Robust Master Mix | 95% | 30.5 | 100% | 32 | 7 |

To sum up, the optimal reactive enzyme system was Gold 360 Master Mix.

| detection procedures type | detection rate of point mutation positive quality control products | detection rate of methylation positive quality control products | false negative number of negative control products |
|---|---|---|---|
| standard qPCR detection procedure | 100% | 85% | 3 |
| the detection procedure of the present disclosure | 100% | 100% | 0 |

To sum up, the optimal reaction detection procedure was the detection procedure of the present disclosure.

Example 4 Detection Limit of the Combined Auxiliary Diagnostic Kit of Gene Point Mutation and Methylation of the Bladder Cancer Driver Genes According to the following table, the point mutation positive plasmid (E10 UI) and the methylation positive plasmid (methylation level 100%) were verified by first-generation sequencing. The negative plasmid was a DNA plasmid (E10 UI) without the above-mentioned detected mutation and unmethylated, and the sample was diluted in gradient, and the quantitative standard curve of point mutation and the standard curve of methylation level were drawn.

| point mutation positive plasmid dilution in gradient | point mutation content (UI/mL) | methylation positive plasmid (methylation level) | statistical method |
|---|---|---|---|
| high concentration | E5 | 50% | The positive |
| medium concentration | E4 | 10% | detection rate |
| low concentration | E3 | 5% | and repeatability |
| | E2 | 7.5% | at different |
| | 50 | 1% | concentrations |
| | 10 | 0.5% | were counted respectively |

According to the gradient dilution in the above table, the positive samples and negative samples with corresponding detection content were prepared, the samples were tested according to the optimal detection method (the parameters of the optimal detection method were as shown in the following table), and the theoretical detection value, actual detection value and CV of positive samples were counted.

The optimal detection reaction system was as follows: Point mutation reaction system:

| component | primer or reagent name | dosage volume or amount of substance |
|---|---|---|
| PCR Mix | 2× Gold 360 Master Mix | 25 μL |
| Probe/primer Mix | FGFR3-ARMS-F4 | 25 μM |
| | FGFR3-ARMS-R | 25 μM |
| | FGFR3-ARMS-FAM | 15 μM |
| | TERT-ARMS-F4 | 25 μM |
| | TERT-ARMS-R | 25 μM |
| | TERT-ARMS-HEX | 10 μM |
| | PLEKHS1-ARMS-F4 | 25 μM |
| | PLEKHS1-ARMS-R | 25 μM |
| | PLEKHS1-ARMS-ROX | 10 μM |
| | ATCB-ARMS-F | 2.5 μM |
| | ATCB-ARMS-R | 2.5 μM |
| | ATCB-ARMS-VIC | 5 μM |
| PCR enhancer | 25× PCR enhancer | 2 μL |
| products to be tested | purified nucleic acid product | 5 μL |
| NF*H$_2$O | NF-H$_2$O | make up to 50 μL |

Gene methylation reaction system:

| component | primer or reagent name | dosage volume or amount of substance |
|---|---|---|
| PCR Mix | 2× Gold 360 Master Mix | 25 μL |
| Probe/primer Mix | OTX1-ARMS-F1 | 25 μM |
| | OTX1-ARMS-R3 | 25 μM |
| | OTX1-ARMS-FAM | 15 μM |
| | NRN1-ARMS-F1 | 25 μM |
| | NRN1-ARMS-R2 | 25 μM |
| | NRN1-ARMS-HEX | 10 μM |
| | NID2-ARMS-F1 | 25 μM |
| | NID2-ARMS-R3 | 25 μM |
| | NID2-ARMS-ROX | 10 μM |
| | ATCB-ARMS-F | 2.5 μM |
| | ATCB-ARMS-R | 2.5 μM |
| | ATCB-ARMS-VIC | 5 μM |
| PCR enhancer | 25× PCR enhancer | 2 μL |
| products to be tested | purified nucleic acid product | 5 μL |
| NF-H$_2$O | NF-H$_2$O | make up to 50 μL |

Optimal detection reaction procedure:

| the first stage | 95° C. | 10 min | 1 cycle | pre-denaturation |
|---|---|---|---|---|
| the second stage | 95° C. | 15 s | 15 cycles | high TM template enrichment |
| | 59° C. | 45 s | | |
| | 72° C. | 1 min | | |
| the third stage | 95° C. | 15 s | 35 cycles | |
| | 55° C. | 45 s | | |
| | 72° C. | 1 min | | collection of the fluorescence signal |
| the fourth stage | 40° C. | 1 min | 1 cycle | cooling |

Standards for determination of negative and positive results:

| detection category | gene name | standards for positive results | standards for negative results | standards for determination of positive results | standards for determination of negative results |
|---|---|---|---|---|---|
| point mutation detection | FGFR3 | Ct < 30.5 | Ct > 30.5 or no Ct value | The results of point mutation test and methylation | The results of point mutation test and methylation |
| | TERT | Ct < 28.5 | Ct > 28.5 or no Ct value | | |

-continued

| detection category | gene name | standards for positive results | standards for negative results | standards for determination of positive results | standards for determination of negative results |
|---|---|---|---|---|---|
| | PLEKHS1 | Ct < 30.5 | Ct > 30.5 or no Ct value | test are at least 1 | test are both negative, the |
| | ATCB | Ct < 36 | Ct < 36 | positive, and | sample is |
| methylation detection | OTX1 | Ct < 30.5 | Ct > 30.5 or no Ct value | the sample is interpreted as | interpreted as negative. |
| | NRN1 | Ct < 28.5 | Ct > 28.5 or no Ct value | positive. | |
| | NID2 | Ct < 30.5 | Ct > 30.5 or no Ct value | | |
| | ATCB | Ct < 36 | Ct < 36 | | |

Test Results

| theoretical value of point mutation positive standard | actual test content | CV % | theoretical methylation level of methylation-positive standard | actual test content | CV % |
|---|---|---|---|---|---|
| 1E5 | 0.98E5 | 0.3 | 50% | 49.75% | 0.1 |
| 1E4 | 0.97E4 | 0.5 | 10% | 9.88% | 0.4 |
| 1E3 | 0.99E3 | 0.8 | 5% | 4.88% | 0.6 |
| 1E2 | 0.97E2 | 1.0 | 2.5% | 2.03% | 1.0 |
| 50 | 49.88 | 1.5 | 1% | 0.91% | 1.2 |
| 10 | — | — | 0.5% | 0.47% | 2.0 |

Example 5 Clinical Trial of the Combined Auxiliary Diagnostic Kit of Gene Point Mutation and Methylation of the Bladder Cancer Driver Genes According to the requirements of clinical trials, 100 cases (53 cases with negative hematuria and 47 cases with positive hematuria) were obtained. Nucleic acid extraction was carried out on urine precipitation samples respectively by using the nucleic acid extraction kits, and 100 ng of urine precipitation nucleic acids were taken for heavy salt transformation (see the instructions for heavy salt transformation operation). 100 clinical samples were tested according to the above-mentioned optimal detection methods (negative and positive interpretation standards in Example 1, the best primers and probes combination in Example 2, and the best detection reaction system in Example 3). The number of true positive, true negative, false positive and false negative samples were counted respectively, and the corresponding specificity and sensitivity performance were counted.

Test Results

Point mutation test results:

| | true positive | false negative | true negative | false positive |
|---|---|---|---|---|
| pathological positive sample | 47 | 40 | 7 | |
| pathological negative sample | 53 | | | 48 | 5 |

Gene methylation test results:

| specificity (%) | sensitivity (%) | positive predictive value (%) | negative predictive value (%) |
|---|---|---|---|
| 85.10 | 90.56 | 88.88 | 87.27 |

| | true positive | false negative | true negative | false positive |
|---|---|---|---|---|
| pathological positive sample | 47 | 38 | 9 | |
| pathologically negative sample | 53 | | | 53 | 0 |

| specificity (%) | sensitivity (%) | positive predictive value (%) | negative predictive value (%) |
|---|---|---|---|
| 80.85 | 100 | 100 | 85.48 |

Point mutation and gene methylation combined test results:

| | true positive | false negative | true negative | false positive |
|---|---|---|---|---|
| Pathological positive sample | 47 | 43 | 4 | |
| Pathologically negative sample | 53 | | | 53 | 0 |

| specificity (%) | sensitivity (%) | positive predictive value (%) | negative predictive value (%) |
|---|---|---|---|
| 91.48 | 100 | 100 | 92.98 |

The above-mentioned is only to explain some embodiments of the present disclosure. Since it is easy for those ordinary technicians in the same technical field to make a number of modifications and changes on this basis, the present disclosure is not intended to limit the present invention to the specific structure, method steps and scope of application shown and described. Therefore, all the corresponding modifications and equivalents that may be utilized belong to the scope of patent applications for the present invention.

What is claimed is:

1. A detection reagent for screening bladder cancer by targeting driver genes related to the pathway of bladder cancer, comprising specific primers and probes designed for detection of regions in a template, wherein the regions to be detected comprise at least one of a gene point mutation or a gene methylation;

wherein the gene point mutation comprises a FGFR3 point mutation, a TERT point mutation, and a PLEKHS1 point mutation, wherein the gene methylation comprises OTX1 methylation, NID2 methylation, and NRN1 methylation, wherein the region to be detected for the FGFR3 point mutation is the sequence set forth in SEQ ID NO: 1; the region to be detected for the TERT point mutation is the sequence set forth in SEQ ID NO: 2; and the region to be detected for the PLEKHS1 point mutation is the sequence set forth in SEQ ID NO: 3, wherein no transformation or sequence alteration of the gene point mutation sequences is required;

wherein the region to be detected for the OTX1 methylation is the sequence set forth in SEQ ID NO: 4; the region to be detected for the NID2 methylation is the sequence set forth in SEQ ID NO: 5; and the region to be detected for the NRNI methylation is the sequence set forth in SEQ ID NO: 6;

wherein the specific primers and probes designed for the regions to be detected in the template are the following primer pairs and probes:

the forward primer, reverse primer, and probe for the FGFR3 point mutation are the sequences set forth in SEQ ID NOs: 10, 11 and 12 respectively;

the forward primer, reverse primer, and probe for the TERT point mutation are the sequences set forth in SEQ ID NOs: 16, 17 and 18 respectively;

the forward primer, reverse primer, and probe for the PLEKHS1 point mutation are the sequences set forth in SEQ ID NOs: 22, 23 and 24 respectively;

the forward primer, reverse primer, and probe for the OTX1 methylation are the sequences set forth in SEQ ID NOs: 25, 29 and 30 respectively;

the forward primer, reverse primer, and probe for the NID2 methylation are the sequences set forth in SEQ ID NOs: 31, 34 and 35 respectively;

the forward primer, reverse primer, and probe for the NRN1 methylation are the sequences set forth in SEQ ID NOs: 36, 38 and 37 respectively;

wherein the detection reagent further comprises primers and a probe designed for an internal reference gene, wherein the internal reference gene is ATCB; and wherein the primers and probe designed for the internal reference gene are the sequences set forth in SEQ ID NOs: 41-43.

2. The detection reagent according to claim 1, wherein the specific primers and probes for detecting the gene point mutation and/or gene methylation are further distributed in different reaction tubes, the reaction tubes are respectively a reaction tube A and a reaction tube B, wherein the reaction tube A is used to detect the gene point mutation point mutations, and a composition thereof is as follows:

| Reagent Name | Reaction Volume (μL) |
| --- | --- |
| Primer&Probe A | 2 |
| 2× Gold 360 Master Mix | 25 |
| PCR enhancer | 1 |
| nucleic acid to be detected | 5 |
| NF-H$_2$O | 17 |
| total volume | 50 | wherein, Primer&Probe A is a mixture composed of the primer pairs and probes for detection of the point mutations in FGFR3\TERT\PLEKHS1 and the internal reference gene primers and probe; and wherein the reaction tube B is used to detect gene methylation, and the composition thereof is as follows:

| Reagent Name | Reaction Volume (μL) |
| --- | --- |
| Primer&Probe B | 2 |
| 2× Gold 360 Master Mix | 25 |
| PCR enhancer | 1 |
| purified nucleic acid after heavy salt transformation | 5 |
| NF-H$_2$O | 17 |
| total volume | 50 | wherein, Primer&ProbeB is a mixture composed of the primer pairs and probes for detection of methylation in OTX1\NRN1\NID2 and internal reference gene primers and probes.

3. The detection reagent according to claim 1, comprising the following components:

| Reagent Name | Effective Components |
| --- | --- |
| Primer&Probe A | A mixture of primer pairs and probes for detection of the point mutations in FGFR3, TERT, and PLEKHS1 and the internal reference gene |

-continued

| Reagent Name | Effective Components |
|---|---|
| Primer&Probe B | A mixture of primer pairs and probes for detection of methylation in OTX1, NRN1, and NID2 and the internal reference gene |
| DNA polymerase Master Mix | DNA polymerase, dNTPs, $Mg^{2+}$, Tris-HCl, NaCl and nuclease-free water |
| PCR enhancer | DTT and/or BSA |
| point mutation positive quality control | adenovirus packaging positive mutant plasmid |
| methylation positive quality control | methylation-positive nucleic acid after methylase transformation |
| negative control | T cells after wild-type plasmid transfection |
| NF-H$_2$O | nuclease-free water | wherein the sequences and concentration of each primer pair and probe in Primer&Probe A are as follows:

the forward primer, reverse primer and probe for the FGFR3 point mutation are the sequences set forth in SEQ ID NOs: 10, 11 and 12, and the concentrations are 25 μM, 25 μM and 15 μM respectively;

the forward primer, reverse primer and probe for the TERT point mutation are the sequences set forth in SEQ ID NOs: 16, 17 and 18, and the concentrations are 25 μM, 25 μM and 10 μM respectively;

the forward primer, reverse primer and probe for the PLEKHSI point mutation are the sequences set forth in SEQ ID NOs: 22, 23 and 24, and the concentrations are 25 μM, 25 μM and 8 μM respectively; and the forward primer, reverse primer and probe for the internal reference gene are the sequences set forth in SEQ ID NOs: 41-43 and the concentrations are 2.5 μM, 2.5μM and 5 μM respectively; and wherein the sequences and concentration of each primer pair and probe in Primer&Probe B are as follows:

the forward primer, reverse primer and probe for the OTX1 methylation are the sequences set forth in SEQ ID NOs: 25, 29 and 30, and the concentrations are 25 μM, 25 μM and 15 μM respectively;

the forward primer, reverse primer and probe for the NID2 methylation are the sequences set forth in SEQ ID NOs: 31, 34 and 35, and the concentrations are 25 μM, 25 μM and 15 μM respectively;

the forward primer, reverse primer and probe for the NRN1 methylation are the sequences set forth in SEQ ID NOs: 36, 38 and 37, and the concentrations are 25 μM, 25μM and 15 μM respectively; and the forward primer, reverse primer and probe for the internal reference gene are the sequences set forth in SEQ ID NOs: 41-43, and the concentrations are 2.5 μM, 2.5 μM and 5 μM, respectively.

* * * * *